United States Patent [19]

Tanaka et al.

[11] Patent Number: 4,937,362
[45] Date of Patent: Jun. 26, 1990

[54] PROCESS FOR PRODUCTION OF α-(4-ISOBUTYLPHENYL)PROPIONIC ACID

[75] Inventors: Kazuo Tanaka; Yoshikazu Shima, both of Niigata, Japan

[73] Assignee: Mitsubishi Gas Chemical Company, Inc., Tokyo, Japan

[21] Appl. No.: 373,238

[22] Filed: Jun. 28, 1989

[30] Foreign Application Priority Data

Sep. 22, 1988 [JP] Japan .................. 63-236219

[51] Int. Cl.$^5$ .............................. C07C 51/12
[52] U.S. Cl. ................................... 562/406
[58] Field of Search .......................... 562/406

[56] References Cited

U.S. PATENT DOCUMENTS

| | | |
|---|---|---|
| 4,134,912 | 1/1979 | Naglieri ........................... 562/406 |
| 4,356,320 | 10/1982 | Naglieri et al. .................. 562/519 |
| 4,426,537 | 1/1984 | Gauthier-Lafaye ............... 562/406 |
| 4,482,497 | 11/1984 | Rizkalla ........................... 562/406 |
| 4,620,033 | 10/1986 | Isshiki ............................. 562/406 |
| 4,625,049 | 11/1986 | Curren ............................. 562/406 |
| 4,659,518 | 4/1987 | Rizkalla ........................... 562/406 |
| 4,843,172 | 6/1989 | Tanaka ............................. 562/406 |

*Primary Examiner*—Michael L. Shippen
*Attorney, Agent, or Firm*—Frishauf, Holtz, Goodman & Woodward

[57] ABSTRACT

A process for production of α-(4-isobutylphenyl)propionic acid is disclosed, comprising reacting α-(4-isobutylphenyl) ethyl alcohol with carbon monoxide in the presence of a three component catalyst comprising (1) a nickel compound, (2) a phosphine compound, and (3) an iodine compound or bromine compound. This reaction is preferably carried out in a solvent comprising aromatic ketones or alicyclic ketones.

15 Claims, No Drawings

PROCESS FOR PRODUCTION OF α-(4-ISOBUTYLPHENYL)PROPIONIC ACID

BACKGROUND OF THE INVENTION

1. Field of the Invention

The present invention relates to a process for production of high purity α-(4-isobutylphenyl)propionic acid and more particularly to a process for producing high purity α-(4-isobutylphenyl)propionic acid with high reactive efficiency and at low cost by the use of a specified catalyst.

2. Description of the Related Arts

α-(4-isobutylphenyl)propionic acid has heretofore been synthesized by various methods using a wide variety of compounds as the starting material. For example, a method of synthesizing α-(4-isobutylphenyl)propionic acid using isobutylacetophenone as the starting material through five steps is known.

The above conventional method, however, fails to produce α-(4-isobutylphenyl)propionic acid at low cost on a commercial scale because (1) it uses an expensive starting material and catalyst, (2) in order to obtain a high purity product, the reaction process inevitably becomes complicated, and (3) the yield at each step is low.

In recent years, a method of synthesizing α-(4-isobutylphenyl)propionic acid or its ester by a one-step process in which p-isobutylstyrene or α-(4-isobutylphenyl)ethyl alcohol as starting material is reacted with carbon monoxide, or carbon monoxide and water or alcohol, has been proposed.

In connection with the case in that p-isobutylstyrene is used as a starting material. Japanese Patent Application Laid-Open Nos. 10545/1984 and 216849/1984 disclose methods using palladium complexes as catalyst. These methods, however, have disadvantages in that (1) it uses a catalyst of palladium which is a relatively expensive noble metal, and (2) p-isobutylstyrene is obtained by dehydration of α-(4-isobutylphenyl)ethylalcohol and since the yield at the dehydration step is not always high, p-isobutylstyrene as the starting material inevitably becomes relatively expensive. These methods have other disadvantages in that many by-products are produced and thus the yield of product is insufficient.

In connection with the case in that α-(4-isobutylphenyl)ethyl alcohol is used as a starting material, Japanese Patent Application Laid-Open No. 242642/1987 discloses a combination catalyst of rhodium and iodine, and Japanese Patent Application Laid-Open No. 263140/1987 discloses use of a mixed solvent of an hydrocarbon and an oxygen-containing organic compound.

These methods, however, have disadvantages in that (1) rhodium which is a markedly expensive noble metal is used as the catalyst, (2) β-(4-isobutylphenyl)propionic acid, which is an isomer difficult to isolate, is by-produced in a considerable amount, and (3) a large amount of polymer is by-produced and thus the yield of α-(4-isobutylphenyl)propionic acid is unsatisfactorily low.

The present inventors made extensive investigations to develop a method of producing α-(4-isobutylphenyl)propionic acid using inexpensive α-(4-isobutylphenyl)ethyl alcohol as a starting material.

SUMMARY OF THE INVENTION

As a result, it has been discovered that the desired α-(4-isobutylphenyl)propionic acid can be produced in a high yield by reacting α-(4-isobutylphenyl)ethyl alcohol with carbon monoxide in the presence of a three component catalyst comprising nickel, phosphine and iodine or bromine, in a specified solvent. The present invention has been developed, based on the findings.

An object of the present invention is to provide a process for efficiently producing α-(4-isobutylphenyl)propionic acid using a relatively inexpensive catalyst and starting material.

Another object of the present invention is to provide a process for producing high purity α-(4-isobutylphenyl) propionic acid by a simplified procedure.

Still another object of the present invention is to provide a process for producing high quality α-(4-isobutylphenyl)propionic acid at low cost.

The present invention relates to a process for producing α-(4-isobutylphenyl)propionic acid which comprises reacting α-(4-isobutylphenyl)ethyl alcohol and carbon monoxide in the presence of a three component catalyst comprising (1) a nickel compound, (2) a phosphine compound and (3) an iodine or bromine compound, in a solvent comprising aromatic ketones or alicyclic ketones.

DESCRIPTION OF THE PREFERRED EMBODIMENTS

The catalyst to be used in the present invention comprises the three components (1), (2) and (3) as described above. As component (1) which is a main catalyst, only nickel (nickel compound) among base metal elements of Group VIII of the Periodic Table, i.e., iron, cobalt and nickel is used. That is, the other elements than nickel can hardly produce α-(4-isobutylphenyl)propionic acid while on the other hand a catalyst containing a nickel element as the main catalyst exhibits dramatic catalytic performance.

The nickel compound, component (1), as the main catalyst in the process of the present invention can be a compound capable of forming a carbonyl compound in the reaction and various nickel compounds can be used. Preferred nickel compounds are metallic nickel, nickel chloride, nickel bromide, nickel iodide, nickel sulfate, nickel acetate, nickel oxide, nickelocene, dicarbonylbis(triphenyl) phosphine nickel, and other similar nickel compounds.

The phosphine compound, component (2), of the catalyst to be used in the process of the present invention acts as a catalyst coordinate. Specific examples of the phosphine compound are triethylphosphine, tri-n-butylphosphine, triphenylphosphine, tricyclohexylphosphine, tribenzylphosphine, bis-1,4-diphenylphosphinobutane, and other tertiary phosphines.

The iodine or bromine compound, the component (3), of the catalyst to be used in the process of the present invention acts as a co-catalyst or a promoter. As the iodine compound; iodine, hydrogen iodide, sodium iodide, potassium iodide, methyl iodide, ethyl iodide, tetramethylammonium iodide, tetramethylphosphonium iodide, and other iodides can be used. In place of the iodine compound. a bromine compound can be used. In this case, bromine, hydrogen bromide, sodium bromide, potassium bromide, methyl bromide, ethyl bromide, tetramethylammonium bromide, and tetramethylphosphonium bromide are preferably used.

As each of components (1), (2) and (3) in preparation of the three component catalyst of the present invention, two or more of the compounds listed above can be used in combination.

In the process of the present invention, although the reaction proceeds in the absence of a solvent, it is preferred that the reaction be carried out in a solvent in order to obtain the desired α-(4-isobutylphenyl)propionic acid in a high yield. Suitable solvents include aromatic ketones and alicyclic ketones. As the aromatic ketones, acetophenone is most suitable. As the alicyclic ketones, cyclohexanone is most suitable.

In the process of the present invention, if the above compounds are used as solvent, a marked solvent effect is exhibited and α-(4-isobutylphenyl)propionic acid can be obtained in a high yield with high selectivity.

On the other hand, if a general acyclic ketone compound, such as acetone, diethyl ketone, methyl ethyl ketone or methyl isobutyl ketone is used as a solvent, α-(4-isobutylphenyl) propionic acid cannot be obtained in a sufficiently high yield.

In the process of the present invention, hydrocarbons such as benzene, toluene, hexane and octane; ethers such as diethyl ether, dioxane and tetrahydrofuran; esters such as methyl acetate and ethyl acetate; and organic acids such as acetic acid and butyric acid can also be used. However, the yield of the desired α-(4-isobutylphenyl) propionic acid is not sufficiently high.

Although the above specified ketones such as acetophenone and cyclohexanone are preferably used as the solvent in the process of the present invention, they can be used as mixed solvents in admixture with other solvents.

The amount of the nickel compound, component (1), used as the main catalyst of the present invention can be determined appropriately depending on various conditions. The amount of the nickel compound used is usually $10^{-5}$ to 10 gram atoms, preferably $10^{-3}$ to 1 gram atom per mol of α-(4-isobutylphenyl) ethyl alcohol. Although the nickel compound can be used in a greater amount, it is not economical, and in smaller amounts, the rate of reaction is undesirably decreased.

The amount of the phosphine compound, component (2), used as the catalyst coordinate of the present invention can also be determined appropriately depending on various conditions. The atomic ratio of phosphine in the phosphine compound to nickel in the nickel compound is usually 0.1 to 20 and preferably 1 to 6. Use of the phosphine compound in a greater ratio is not economical. On the other hand, if the atomic ratio is too small, the yield and selectivity of α-(4-isobutylphenyl)propionic acid are undesirably decreased.

The amount of the iodine compound or bromine compound, component (3), used as the co-catalyst of the present invention can also be determined appropriately depending on various conditions. The atomic ratio of the iodine compound or bromine compound to the nickel compound is usually 0.1 to 100 and preferably 1 to 20. Although the iodine compound or bromine compound can be used in a larger amount, it is not economical. If the amount of the iodine compound or bromine compound used is too small, the rate of reaction is undesirably decreased.

In the process of the present invention, it is preferred, as described above, that the reaction be carried out in the presence of a solvent. The amount of a ketone compound such as acetophenone or cyclohexanone to be used as a solvent is not critical, usually nor more than 100 parts by weight, and preferably 1 to 20 parts by weight per part by weight of α-(4-isobutylphenyl)ethyl alcohol. Although the ketone compound can be used in a larger amount, it is not economical.

The reaction temperature is 50 to 300° C., with the range of 150 to 250° C. being preferred for practical use. If the reaction temperature is too low, the reaction proceeds only insufficiently, and if it is too high, the amount of byproducts increases.

The reaction pressure is, as a carbon monoxide partical pressure, 5 to 500 kg/cm$^2$ and preferably 10 to 200 kg/cm$^2$. Carbon monoxide partial pressures higher than 500 kg/cm$^2$ are unsuitable from a practical standpoint. On the other hand, if the carbon monoxide partial pressure is less than 5 kg/cm$^2$, the yield of α-(4-isobutylphenyl)propionic acid is undesirably decreased.

Carbon monoxide to be used in the present invention can be mixed with an inert gas such as nitrogen or methane.

The reaction period cf time can be determined depending on conditions such as the type and amount of starting material, catalyst, solvent and so on which are to be supplied, reaction conditions such as temperature and pressure, and further on the reaction style and so on. The reaction period of time is usually 0.3 to 20 hours and preferably 0.3 to 5 hours.

In connection with the reaction style of the process of the present invention, it can be carried out batchwise or continuously. The α-(4-isobutylphenyl)propionic acid formed is separated and purified by operations such as distillation. extraction, crystallization and recrystallization.

In accordance with the process of the present invention, α-(4-isobutylphenyl)propionic acid can be produced in a high yield and at low cost by using relatively inexpensive α-(4-isobutylphenyl)ethyl alcohol as a starting material and reacting it with carbon monoxide by a one-stage process, without use of an expensive noble metal catalyst.

α-(4-isobutylphenyl)propionic acid obtained by the process of the present invention can be used in preparation of useful medicines having antiphlogistic, lenitive and antifebrile actions.

The present invention is described in greater detail with reference to the following examples, although it is not intended to be limited thereto.

In the examples, the product was identified and quantitatively determined by a proton nuclear magnetic resonance ($^1$H-NMR) spectral analysis and gas chromatography.

EXAMPLE 1

Four point zero grams of α-(4-isobutylphenyl)ethyl alcohol, 0.47 g of nickel iodide, 0.59 g of triphenyl phosphine, 0.32 g of methyl iodide and 10.0 g of acetophenone as a solvent were placed in a 100-milliliter shaking autoclave made of Hastelloy C. Carton monoxide was introduced under pressure so that the carton monoxide partial pressure reached 100 kg/cm$^2$, and reacted at 170° C. for 2 hours.

After the reaction was completed, the autoclave was cooled and the residual gas was purged. Then the liquid product was analyzed by gas chromatography (internal standard method).

The conversion of α-(4-isobutylphenyl)ethyl alcohol was 99.0%, and the selectivity to α-(4-isobutylphenyl)-propionic acid was 81.2%.

EXAMPLE 2

The procedure of Example 1 was repeated with the exception that as the phosphine, 0.45 g of tri(n-butyl) phosphine was used in place of triphenylphosphine.

The conversion of α-(4-isobutylphenyl)ethyl alcohol was 99.2%, and the selectivity to α-(4-isobutylphenyl)-propionic acid was 80.4%.

EXAMPLE 3

The procedure of Example 1 was repeated with the exception that as the phosphine, 0.63 g of tricyclohexyl phosphine was used in place of triphenylphosphine.

The conversion of α-(4-isobutylphenyl)ethyl alcohol was 99.1%, and the selectivity to α-(4-isobutylphenyl)-propionic acid was 87.4%.

EXAMPLE 4

The procedure of Example 1 was repeated with the exception that as the solvent, cyclohexanone was used in place of acetophenone.

The conversion of α-4-isobutylphenyl)ethyl alcohol was 98.6%, and the selectivity to α-(4-isobutylphenyl)-propionic acid was 79.3%.

EXAMPLE 5

The procedure of Example 1 was repeated with the exception that 2.0 g of hexane in addition to acetophenone as the solvent were used.

The conversion of α-(4-isobutylphenyl)ethyl alcohol was 99.6%, and the selectivity to α-(4-isobutylphenyl)-propionic acid was 81.7%.

COMPARATIVE EXAMPLE 1

The procedure of Example 1 was repeated with the exception that triphenylphosphine was not added. Almost none of the desired α-(4-isobutylphenyl)propionic acid was formed.

COMPARATIVE EXAMPLE 2

The procedure of Example 1 was repeated with the exception that acetophenone as a solvent was not added. Almost no desired product was formed.

COMPARATIVE EXAMPLE 3

The procedure of Example 1 was repeated with the exception that 0.35 g of cobalt iodide was used in place of nickel iodide. The conversion of the starting material was 48.5%, and the selectivity to the desired product was 1.2%.

COMPARATIVE EXAMPLE 4

The procedure of Example 1 was repeated with the exception that 0.35 g of iron iodide was used in place of nickel iodide. The conversion of the starting material was 37.4%, and the selectivity to the desired product was 0.2%.

COMPARATIVE EXAMPLE 5

The procedure of Example 1 was repeated with the exception that as the solvent, acetone was used in place of acetophenone. The conversion of the starting material was 99%, and the selectivity to the desired product was 37.8%.

COMPARATIVE EXAMPLE 6

The procedure of Comparative Example 5 was repeated with the exception that 2 g of hexane in addition to acetone as the solvent were used. The conversion of the starting material was 99.2%, and the selectivity to the desired product was 36.5%.

COMPARATIVE EXAMPLE 7

The procedure of Example 1 was repeated with the exception that as the solvent, hexane was used in place of acetophenone. The conversion of the starting material was 88.5%, and the selectivity to the desired product was 7.3%.

COMPARATIVE EXAMPLE 8

The procedure of Example 1 was repeated with the exception that as the solvent, dioxane was used in place of acetophenone. The conversion of the starting material was 97.0%, and the selectivity to the desired product was 14.2%.

COMPARATIVE EXAMPLE 9

The procedure of Example 1 was repeated with the exception that as the solvent, benzene was used in place of acetophenone. The conversion of the starting material was 95.2%, and the selectivity to the desired product was 10.5%.

COMPARATIVE EXAMPLE 10

The procedure of Example 1 was repeated with the exception that as the solvent, acetic acid was used in place of acetophenone. The conversion of the starting material was 96.0%, and the selectivity to the desired product was 5.1%.

COMPARATIVE EXAMPLE 11

The procedure of Example 1 was repeated with the exception that as the solvent, phenyl acetate was used in place of acetophenone. The conversion of the starting material was 96.7%, and the selectivity to the desired product was 14.8%.

What is claimed is:

1. A process for producing α-(4-isobutylphenyl)propionic acid which comprises reacting α-(4-isobutylphenyl)ethyl alcohol with carbon monoxide in the presence of a three component catalyst comprising (1) a nickel compound, (2) a phosphine compound and (3) an iodine compound or bromine compound, in a solvent comprising aromatic ketones or alicyclic ketones.

2. The process as claimed in claim 1 wherein the nickel compound (1) is at least one selected from metallic nickel, nickel chloride, nickel bromide, nickel iodide, nickel sulfate, nickel acetate, nickel oxide, nickelocene, and dicarbonyl bis(triphenyl)phosphine nickel.

3. The process as claimed in claim 1 wherein the phosphine compound (2) is at least one selected from triethylphosphine, tri(n-butyl)phosphine, triphenylphosphine, tricyclohexylphosphine, tribenzylphosphine, and bis-1,4-diphenylphosphinobutane.

4. The process as claimed in claim 1 wherein the iodine compound (3) is at least one selected from iodine, hydrogen iodide, sodium iodide, potassium iodide, methyl iodide, ethyl iodide, tetramethylammonium iodide, and tetramethylphosphonium iodide.

5. The process as claimed in claim 1 wherein the bromine compound (3) is at least one selected from bromine, hydrogen bromide, sodium bromide, potassium bromide, methyl bromide, ethyl bromide, tetramethylammonium bromide, and tetramethylphosphonium bromide.

6. The process as claimed in claim 1 wherein the amount of the nickel compound (1) used is $10^{-5}$ to 10 gram atoms per mol of α-(4-isobutylphenyl)ethyl alcohol.

7. The process as claimed in claim 2 wherein the amount of the nickel compound (1) used is $10^{-5}$ to 10 gram atoms per mol of α-(4-isobutylphenyl)ethyl alcohol.

8. The process as claimed in claim 1 wherein the amount of the phosphine compound (2) used is 0.1 to 20 times (atomic ratio) the nickel atom of the nickel compound (1).

9. The process as claimed in claim 3 wherein the amount of the phosphine compound used is 0.1 to 20 times (atomic ratio) the nickel atom of the nickel compound (1).

10. The process as claimed in claim 1 wherein the amount of the iodine compound or bromine compound (3) used is 0.1 to 20 times (atomic ratio) the nickel atom of the nickel compound (1).

11. The process as claimed in claim 4 wherein the amount of the iodine compound (3) used is 0.1 to 100 times (atomic ratio) the nickel atom of the nickel compound (1).

12. The process as claimed in claim 5 wherein the amount of the bromide compound (3) used is 0.1 to 100 times (atomic ratio) the nickel atom of the nickel compound (1).

13. The process as claimed in claim 1 wherein the reaction temperature is 50 to 300° C. and the reaction pressure is, as carbon monoxide partial pressure, 5 to 500 kg/cm².

14. The process as claimed in claim 1 wherein the aromatic ketones is acetophenone.

15. The process as claimed in claim 1 wherein the alicyclic ketones is cyclohexanone.

* * * * *